Figure 1:
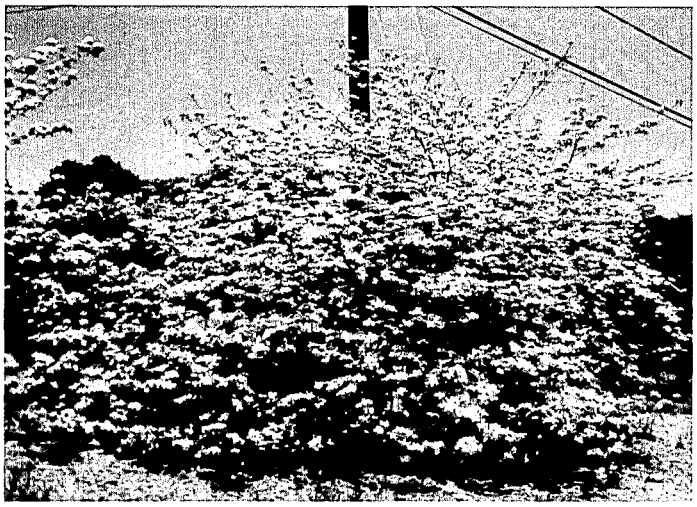

United States Patent [19]

Orton, Jr.

[11] Patent Number: Plant 7,206

[45] Date of Patent: Mar. 27, 1990

[54] DOGWOOD TREE 'STARDUST'

[75] Inventor: Elwin R. Orton, Jr., Somerville, N.J.

[73] Assignee: Rutgers University, New Brunswick, N.J.

[21] Appl. No.: 262,684

[22] Filed: Oct. 26, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

A hybrid of *Cornus kousa* and *Cornus florida* providing a new large-bracted dogwood, which is a vigorous, highly floriferous, small, flowering tree, more nearly like *C. florida,* the plant being low and spreading rather than upright as *C. kousa,* yet more densely branched and foliaged close to the ground as compared with *C. florida* and having a flowering period intermediate that of the parental species.

2 Drawing Sheets

BACKGROUND OF THE INVENTION

This invention relates to a large-bracted dogwood, which is the result of an extensive program of interspecific hybridization to produce certain characteristics which I believe are desirable in dogwood trees and in fact have established this one as an example of a series of dogwood trees, which embody my own concept as to desirability and other characteristics which make the same commercially desirable and thus potentially for widespread dissemination and use by the public.

During the course of my development, I have used an unnamed seedling of *Cornus kousa* Hance as the seed parent and the pollen parent *Cornus florida* L. cv. Cherokee Princess, none of the above being patented.

Some of the characteristics which I have hoped to provide and which this particular cultivar does in fact exemplify, are the novel floral characteristics and growth habit which are due to the hybrid nature of the plant.

Since this particular tree is one of a group, which will be further referred to and is distinct from either of the parents, I have chosen to use the name. 'Rutfan' as the basis for its distinction in the trade and as such the same will be known in commerce by that name.

This hybrid is, I believe, entirely new in horticulture and botany, as to make it necessary to compare only with the parental species as opposed to other cultivars, since the latter do not exist as far as I am aware.

It is important to note the aspect of the overwintering buds of my new cultivar, as compared with the parent plants, noting that the peduncle supporting an overwintering flower bud of *C. florida* is elongated such that the bracts on the peduncle are positioned well below the flower head and that the true flowers are well developed and are tightly enclosed overwinter by two sets of opposing floral bracts that persist in the spring and enlarge to provide the floral display. However, in *C. kousa,* the peduncle supporting an overwintering flower buds is very short, the flowers in the flower head are not well developed, the two sets of opposing floral bracts that clasp the true flowers are minute, and the flowers are tightly enclosed overwinter by the uppermost set of bracts on the peduncle. These bracts drop quickly in the spring as the peduncle begins to elongate and the various components of the flower head enlarge and/or resume development. Plants of *C. kousa* flower a month later in the spring than do plants of *C. florida* since the short peduncle. Relatively undeveloped flowers, and the minute floral bracts require that much more time to mature developmentally.

In the hybrid of the instant cultivar, an intermediate condition between *C. florida* and *C. kousa* prevails in that the peduncle supporting an overwintering flower bud of my hybrid is elongated such that the upper set of bracts is positioned on the peduncle a short distance below the flower head but still close enough to partially enclose the flower head overwinter, along with the fairly well developed floral bracts which enclose the true flowers about 96–99% but not as fully, or tightly, enclosed as is the case in *C. florida.* Thus the overwintering flower buds in my hybrid are partially protected overwinter by both the bracts, which drop early in the spring, and by the floral bracts which persist and enlarge to provide the floral display.

In summary, it may be stated that my new hybrid represents a new large-bracted dogwood, hybrids of the species *C. kousa* and *C. florida* never having been reported previously as far as I know. My new dogwood is a vigorous and highly floriferous, small, flowering tree which develops a form or outline more nearly like plants of the parental American species, *C. florida* rather than being upright as is true for most plants of *C. kousa.* Typically however plants of my new cultivar are more densely branched and foliaged close to the ground than are plants of *C. florida.*

Thus the plants of my new cultivar are intermediate to those of the two parental species with regard to such horticultural characteristics as vigor, branch diameter, time of flowering and of floral display (floral bracts), number of flower heads per tree, number of true flowers per flower head, length of peduncle and size of overwintering flower buds. Additionally position of bracts on the peduncle of the overwintering flower buds and size and stage of development of the true flowers and the floral bracts in the overwintering flower buds are different.

My new hybrid is highly sterile.

In order to summarize the various characteristics which are notable in my cultivar, I have broken down the various aspects of the same as respects its tree shape, flower buds, bracts and other characteristics as will be set forth hereinafter in the specific succinct summaries noted below.

FIG. 1 discloses a tree of my new cultivar in full bloom.

Figure 2:
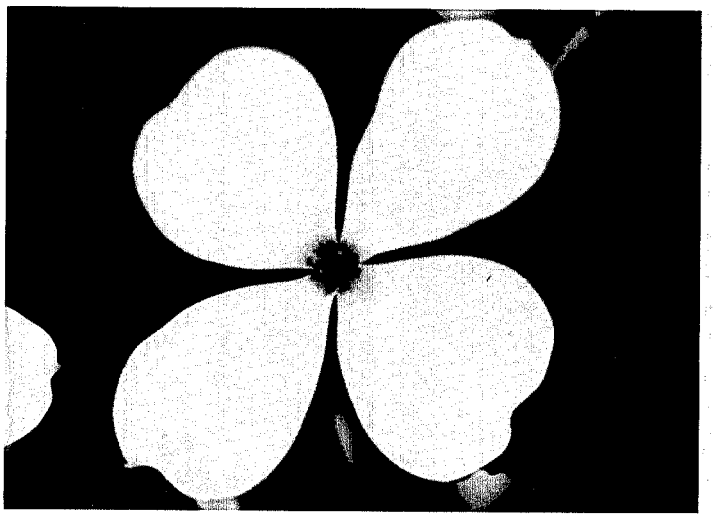

FIG. 2 discloses four floral bracts with central subtended flower heads typical of my new cultivar.

Where color is referred to, The Royal Horticultural Society Colour Chart is availed of and the colors are as nearly true as is possible to make the same in an illustration of this character, made by photographic means.

Tree: The tree disclosed in FIG. 1 of the drawing is about 17 years old, is 3 meters tall and has a spread of 5.3 meters, and I thus describe it as follows: Small; low and spreading; vigorous; dense-topped; hardy; very productive; i.e., very floriferous (but highly sterile); regular bloomer.

Trunk: Medium; smooth when young, but becoming shaggy with age, as then exhibits exfoliating bark.

Branches: Medium; smooth.

Lenticels: Numerous; medium.

Leaves: Abundant; length — 8.0–14.6 cm. (average=11.3). width — 3.5–7.4 cm. (average=5.65) at widest point. Medium size; elliptic; acuminate tip; cuneate to oblique base; medium thickness; dark green; upper surface R.H.S. Colour Chart 139A (Green Group) — lower surface 138B-(Green Group).

Margin: Crenate.

Petiole: Short, 7–17 mm (average=12.3) — medium.

Flower buds: (The true flowers are small and numerous and are borne in flower heads. They are relatively inconspicuous. The floral display is provided by large floral bracts that subtend the flower heads. In common terminology and usually in the art, the floral bracts are described as though they were the flowers.) Hardy; in U.S.D.A. Plant Hardiness Zone 6a (−10 degrees F.). Medium size (larger than those of *C. kousa* but smaller than those of *C. florida;* plump; covered with light brown pubescence.

Floral bracts:

*Color.*—Upper surface-Start of floral display — R.H.S. Yellow Green Group 150D. Midseason floral display — R.H.S. Green-White Group-157A. Peak of floral display — R.H.S. Green-White Group-157B. Lower surface — R.H.S. Green-White Group 157C throughout.

*Size.*—Intermediate in size to those of typical plants of *C. kousa* and *C. florida.* When the floral bracts are fully expanded, the diameter of the inflorescence from tip to tip of the opposing inner bracts is about 101 mm; the diameter of the inflorescence as measured from tip to tip of the opposing outer bracts is about 91 mm. The average length of the inner bracts is approximately 48 mm. The average length of the outer bracts is approximately 42.4 mm. The average width of the inner bracts at their widest point is 33 mm. The average width of the outer bracts at their widest point is 34 mm. Bract length and width will vary from year to year but the inner bracts most likely will be longer and narrower than the outer bracts each year. The shape of the bracts is described as sessile, obovate with acute tips. The margins of adjacent bracts do not touch or overlap except at the points of basal attachment. The inner bracts are longer and narrower than the outer or lower bracts.

*Peduncle length.*—Each flower head is borne on a peduncle, the average length being about 41 mm. at the time of flowering; whereas those of the *C. kousa* parent average 73 mm. in length and those of the *C. florida* parent average 27 mm. at the time of flowering. While absolute peduncle length varies from year to year, the relative peduncle length among the two parents and the hybrid should remain consistent.

Tree:

*Flowers.*—Anthesis of the tiny, relatively inconspicuous true flowers generally commences two to four days following the onset of the ornamental display of the large floral bracts. The average number of true flowers per flower head (30) in this new hybrid is intermediate to that for the *C. kousa* parent (average=49) and that for the *C. florida* parent (average=26). Flowering period is early compared with plants of *C. kousa* and late compared with plants of *C. florida.* Period of floral display (floral bracts) is intermediate to that of plants of the parent species; i.e., occurs in mid-May, commencing one to two days prior to, or just after, completion of the floral display (floral bracts) of most plants of *C. florida* and ending three to six days prior to the onset of the floral display (floral bracts) of most plants of *C. kousa.*

*Fruit.*—Fully developed fruit have not been observed, as plants of this new $F_1$ interspecific hybrid are highly sterile. However, the flower heads often persist throughout the growing season and, occasionally, the fleshy portion of small parthenocarpic (seedless) fruit will develop, albeit incompletely. However, there is no formation of a syncarp as in *C. kousa,* as the flowers in this new hybrid are distinct and separate in the flower head, or on the receptacle.

Resistance to:

*Insects.*—Good. In field plantings with *C. kousa* and *C. florida,* the Dogwood Borer has ravaged the plants of *C. florida,* but has not infested plants of my new $F_1$ interspecific hybrid.

*Disease.*—Good. In field plantings with *C. florida* and *C. kousa,* my new $F_1$ interspecific hybrid has been free of the "dogwood decline" that has decimated cultivated and wild stands of *C. florida* in recent years.

I claim:

1. A new and distinct dogwood tree cultivar, substantially as herein shown and described, characterized particularly as to novelty by the unique combination of its vigor and highly floriferous small flowering form similar to its pollen parent *C. florida* as to its low and spreading shape, densely branched and foliaged arrangement, and intermediate the two parent species as respects the characteristics of the overwintering flower buds, and time of flowering, this hybrid being highly sterile, and resistant to disease and insects.

* * * * *

UNITED STATES PATENT AND TRADEMARK OFFICE

CERTIFICATE OF CORRECTION

PATENT NO. : Plant 7,206

DATED : March 27, 1990

INVENTOR(S) : Elwin R. Orton, Jr.

It is certified that error appears in the above-identified patent and that said Letters Patent is hereby corrected as shown below: On the title page, Item [54] and Column 1, In the Title, 'STARDUST' should read –'RUTFAN'–.

Signed and Sealed this

Sixth Day of July, 1999

*Attest:*

*Attesting Officer*

Q. TODD DICKINSON

*Acting Commissioner of Patents and Trademarks*